United States Patent [19]

Edwardson

[11] Patent Number: 4,695,252
[45] Date of Patent: Sep. 22, 1987

[54] QUICK MOUNT FACE-BOW DEVICE FOR AN ARTICULATOR
[75] Inventor: Svante R. Edwardson, Solna, Sweden
[73] Assignee: AB Dentatus, Hagersten, Sweden
[21] Appl. No.: 804,635
[22] Filed: Dec. 5, 1985
[51] Int. Cl.$^4$ .............................................. A61C 19/04
[52] U.S. Cl. ....................................................... 433/73
[58] Field of Search ........................ 433/73, 56, 69, 68
[56] References Cited

U.S. PATENT DOCUMENTS

| | | | |
|---|---|---|---|
| 2,579,111 | 12/1951 | Fleischhacker | 433/73 |
| 3,084,438 | 4/1963 | Goodfriend | 433/73 |
| 4,330,277 | 5/1982 | Beu | 433/73 |

Primary Examiner—Robert Peshock
Attorney, Agent, or Firm—Young & Thompson

[57] ABSTRACT

A face-bow device for registration of a patient's face and for transferring the registration to an articulator, for use in making dentures or parts thereof, comprises a bite fork on a bite fork support, an adjustment structure in which bite fork support is insertable, and a bow extending from ear to ear in front of the patient's face, on which bow the ajustment structure is mountable. The bow has two arms fixedly connected to each other. Each arm has its free end formed and adapted to be placed in the patient's ear meatus. The arms have a rounded form and are made of a resilient material in order to make them resiliently outbendable at least to such an extent that the bow having its free ends at a distance from each other suitable to the distance between the openings to the patient's ear meatuses in outbent condition is movable over the sides of the patient's face in order to place the ear bow ends into the patient's ear meatuses.

12 Claims, 5 Drawing Figures

QUICK MOUNT FACE-BOW DEVICE FOR AN ARTICULATOR

The present invention relates to a face-bow device for cooperation between a human being and an articulator, for use in making dentures or parts thereof.

In making dentures or parts thereof accurate registrations obtained from the patient must be transferred to the articulator on which the maxillary and mandibular cast are mounted. The jaw mechanism of a human is not a rigid mechanical system, but contains differently yielding tissues. An articulator reproduces the position of the maxilla in relation to the hinge axis and the mandible movement in relation thereto.

In order to have a good fit of the dentures for the patients in question, the individual face dimensions must be considered. Accurate registrations obtained from the patient must be transferred to the articulator with precision. The registrations for the upper cast are preferably don with a face-bow device designed for obtaining precise data from the patient and accurately feeding this information into the articulator.

The hinge axis location for the jaws in humans is situated ca 12 mm in front of the ear meatus, Often the face-bow devices have condylar rods which are placed at this location when obtaining registrations from the patient. However, in recent years it has been customary to place the condylar rods on the face-bow device in the ear meatuses of the patient and then to place the condylar rods on a so-called auditory pin on the condylar track assembly of the articulator instead of directly on the condylar axis pin. The auditory pin is placed 12 mm behind the centrum of the condylar axis pin. This makes the registration procedure more comfortable for the patient and easier and quicker for the operator, who mostly is a dentist.

The invention relates to a face-bow device preferably of this ear hinged type and has as its main purpose to provide very rapid monting on the patient, but it can also relate to a face-bow device for registration from the normally hinged axis points using special end pieces.

There are quick mount face-bow devices on the market of principally two different types. In the first type, two stiff bow halves are connected together in the front of the patient with a pivoting joint, which is locked by the operator when he has placed the face-bow device on the patient in a position such that the ear pieces are seated at the patient's ears. In the second type, two practically straight stiff rods, each having an ear piece in one end, are connected together at the other end by a third stiff rod being extendable by rotating a thumb-wheel. The operator twirls this thumb-wheel in one direction to close the bow to insert the ear pieces in the patient's ears and in the other direction to open it. The disadvantage with these types of face-bows is that the adjustment of the bow to insert the ear pieces in the patient's ears is made while the face-bow device is put on the patient.

The main purpose of the invention is to provide a face-bow, wherein the adjustment of the bow so that the ear pieces will fit into the patient's ears, is made before the bow is actually placed on the patient.

According to the invention this purpose is accomplished by providing a face-bow device, which includes a bite fork on a bite fork support, an adjustment means, in which said bite fork support is insertable, a bow means extending from ear to ear in front of said patient's face, on which bow means said adjustment means is mountable, said bow means having two arms being firmly connected to each other, each arm having its free end formed and adapted to be placed in said patient's ear meatus, said face-bow device being characterized in that said arms have a rounded form and are made of a resilient material in order to be resiliently outbendable at least to such extent that a bow means having its free ends at a distance from each other adapted to the distance between the opening to said patient's ear meatuses in outbent condition is movable over the sides of said patient's face for placing said ear bow ends into said patient's ear meatuses.

Nowadays, face-bow devices having the registered data from patients are mostly sent by mail from the operator, who mostly is a dentist, to some dental laboratory, where dental technicians place them in articulators to make the dentures. Therfore, some modern face-bow devices have the bite fork with the adjusted part of the face-bow removable from the actual bow part after registration on the patient. Only the adjusted part with the bite fork need to be sent the laboratory. This part is not bulky, which means that it can be sent in a smaller package.

When the adjusted part is detachable from the bow part there is only a need to mount the adjusted part with the bite fork as such in a particular jig on the articulator, i.e. without the bow part, when mounting the upper cast from the face-bow registration on the articulator.

According to a further development of the face-bow device according to the invention, the adjusted part has as its main part a pin which has a guidance form at each end, one end fitting against the bow part and being provided with means to lock the pin and the bow part detachably but firmly together at a strictly predetermined relative configuration and orientation, and the other end fitting against a jig means connected to the lower part of the articulator. The other end of the pin is provided with means to lock the pin on the jig means on the plate together at a location and in an orientation, which is the same as if the pin had been connected to the bow part and the bow part were placed on the articulator with its ear pieces at the auditory pins or on the condylar axis.

Still another problem with ordinary face-bow devices is that if the bow device is of the kind, for which the bow part at registration is to be adjusted to be seated in the orbital plane, the adjustment arrangement for this is such that the operator must use both his hands for the adjustment. Such an adjustment arrangement is sometimes a nose support device connectable to the face-bow at registration, the support aligning to the juncture of the upper portion of the nose and the forehead.

According to still another feature of the invention, the nose support device includes a nose resting means, a holding means having a first and a second arm extendable by manual adjustment, said arms having a predetermined angle of less than 90 degrees between their orientations, a means on said first arm to attach said first arm to said bow device, said second arm being connected to said nose resting means. A locking device is provided on the first arm to lock it in an upright position. The first arm has an extendable part in relation to the locking device having a thumb wheel to be rotated by an operator for extension or reduction of the arm length. The sloping arm includes a rather soft spring biased to push the end of the sloping part in the protruding direction and a locking screw to lock the extension of the sloping arm at the desired protruding length. Before the face-bow device is placed on a patient, the end of the sloping arm is pushed in to its innermost position and the locking screw locked.

The invention will now be described with reference to the accompanying drawings, wherein FIG. 1 is a side view, partly in section, of an embodiment of a face-bow device according to the invention;

In the embodiment of the invention shown in FIGS. 1 to 5 the face-bow device includes a bow means 1, which is a bar bent like a bow and made of a resilient material. The bow means 1 is made in one piece, which is to be preferred, and has such dimensions that it extends in front of a person's face from one ear to the other. The end sections of the bow means are bent to point towards each other and are straight. An ear piece 2 is placed on each end section of such size as to be comfortable to the patient when placed in the patient's ear at the opening of the ear canal.

The bow form and the resilient material are chosen in order to make the bow arms resiliently outbendable to a maximum extent which can be chosen between 10 mm and 50 mm, preferably ca 25 mm. The bow means 1 can for instance be made by a bar of harddrawn aluminum or of spring steel.

No investigations have actually been made of the deviation of the distance between the external auitory ear meatuses in adult human beings from a mean distance. As seems to be the case, a deviation from this distance of more than a few millimeters up to ca 10 mm is very rare. Therefore, it could be quite possible to have ear pieces mounted in fixed relation to the bow means ends. However, the ear pieces 2 shown in FIG. 3 are displaceable on the end of the bow means between two extreme limits.

Figure 3:
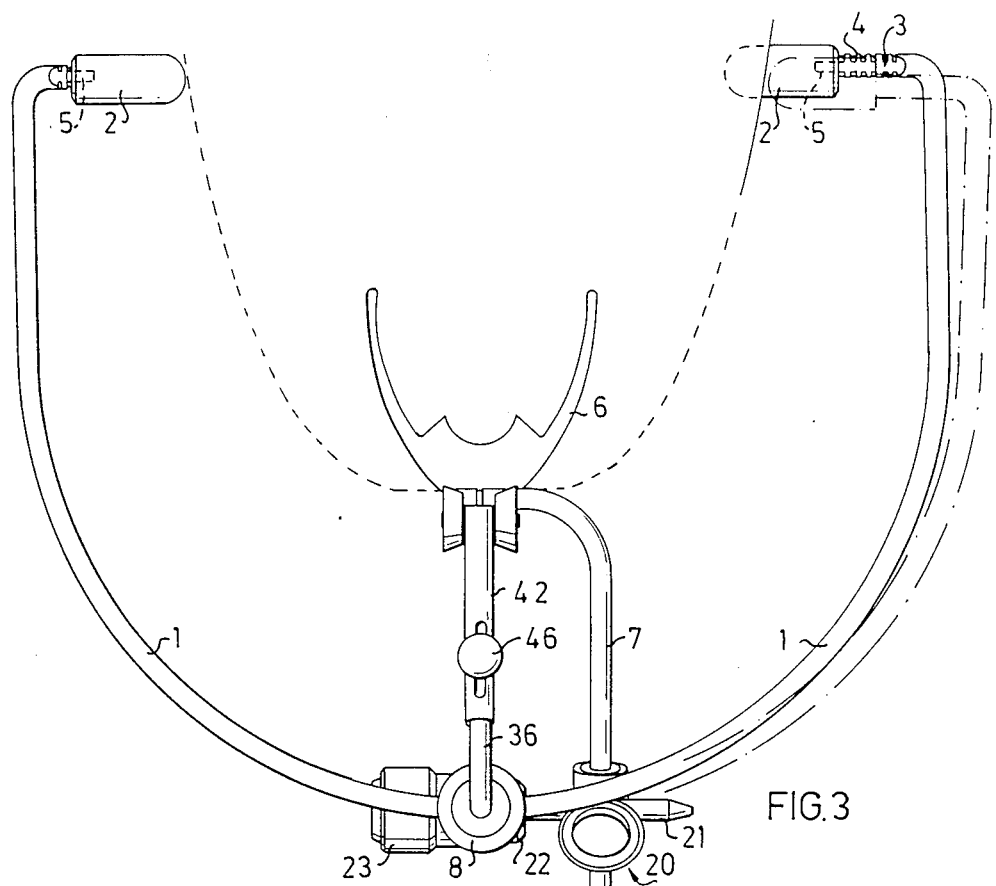
FIG. 3 is a view from above of the face-bow device in FIG. 2.

On the left side of FIG. 3 the ear piece 2 is shown in a position, in which it just touches the skin of the patient in front of the ear. At A, the protrusion of the ear piece is indicated when it is positioned for the largest possible distance to the opposite ear piece, i.e. in its innermost position.

On the right side in FIG. 3 the ear piece 2 is shown in a position, in which it is to be placed in the patient's ear meatus. The bent out position is shown in dashed lines and the bow means postion when seated on the patient is shown in solid lines on the right side of FIG. 3.

From the right side of FIG. 3 it is also apparent that the end of the bow proper is provided with a longitudinal notch or flat ground cut 3 and a plurality of lateral notches 4 extending from the longitudinal notch 3. The ear piece 2 is provided with an inwardly extending, transverse lip 5 adapted to the depth of the notches 3 and 4. In this way the ear piece, if necessary, can be moved longitudinally by rotating the rod to have the lip over the notch 3 and be locked in stepwisely chooseable positions by turning the ear piece when properly positioned. The distance between the lateral notches is for instance 2.5 mm. The lip is suitably slightly resilient and the uttermost part of the end of the bow proper provided with a ringformed rib (not shown). In this way the ear piece is easily detachable from the bow means and can be sterilized or exchanged between measurements on different patients. This possibility can of course be provided in some other way.

In order to be able to mount the face-bow means properly on the patient, if the ear pieces happen not to be correctly set for the patient in question, the operator takes the following mounting steps:

Adjusting the ear pieces for largest possible distance between their opposite front ends. Moving the face-bow on to the patient. Estimating the space between the front ends of the ear pieces and the skin of the patient at the centric relation position. Removing the face-bow from the patient and adjusting the ear pieces first so that they can touch the skin at the centric position and then out 7.5 or 10 mm (3 to 4 notches) on each side (see the right side of FIG. 3). Then the face-bow can be expanded against its spring action and be placed on the patient in the external auditory meatus.

The ear pieces are thus adjusted before the face-bow actually is placed on the patient. This is a great advantage both with regard to the patient's comfort and with regard to ease of operation for the operator.

the embodiment shown in FIGS. 1 to 5 is of a type in which the bow means 1 is to be placed in the so-called orbital plane of the patient, which is the plane going through the hinge axis and orbital points situated just under the eyes. Therefore, a bite fork pin 7 with a bite fork 6 is mountable in an adjustment means placed under the bow means 1 and adjustable vertically, inwardly towards the patient's mouth and to varying slope angles.

According to a further development of the invention use can be made by the fact that the bow means 1 preferably is a rod made in one piece. For this purpose the adjustment part and its detachable mounting on the bow means 1 and also on a jig means 32 on the articulator can have the following design:

For mounting the adjustment means a support 8 is fixedly provided at the middle of the bow and in a predetermined orientation, suitably 90°, to the bow plane.

Figure 1:
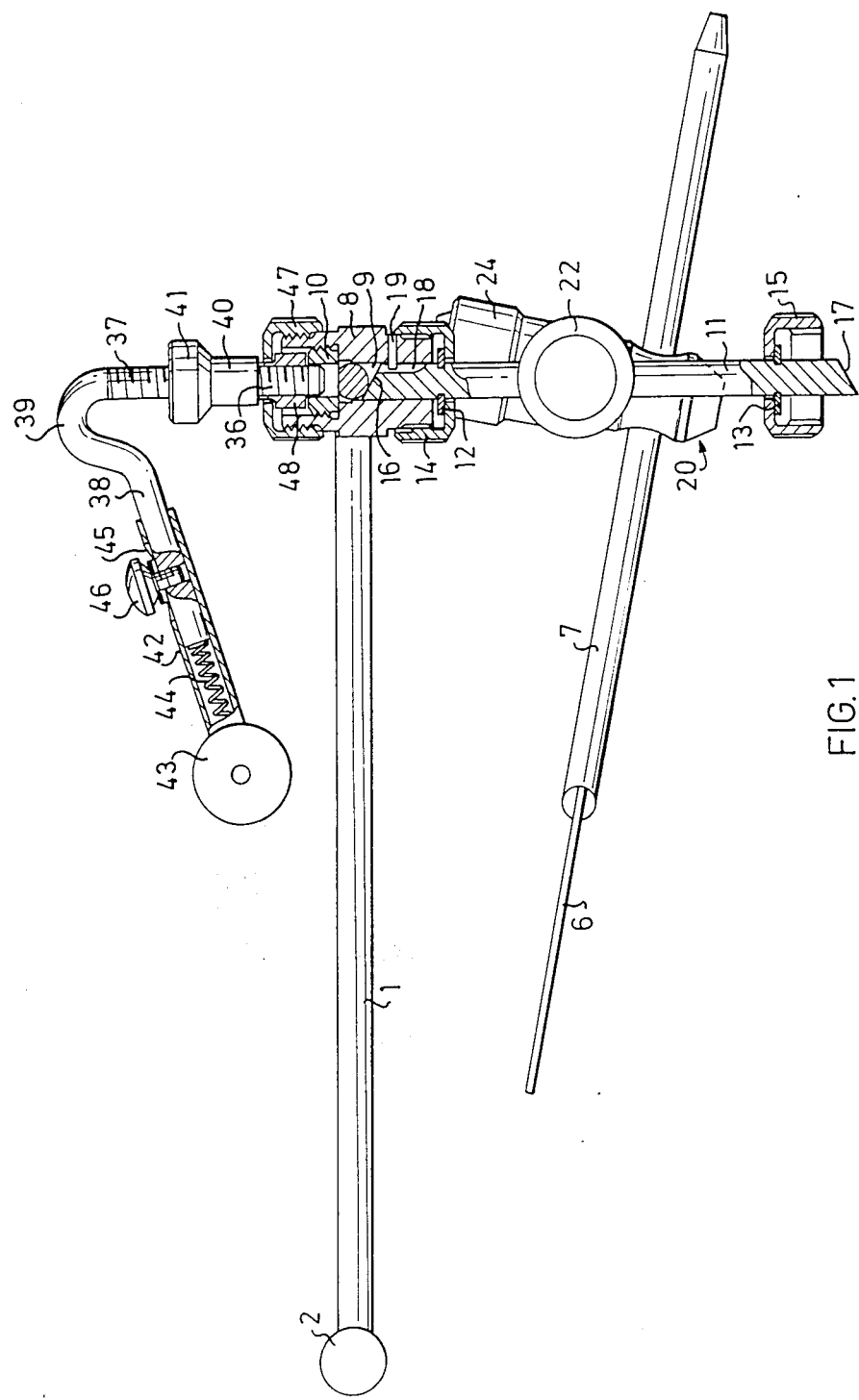
Figure 4:
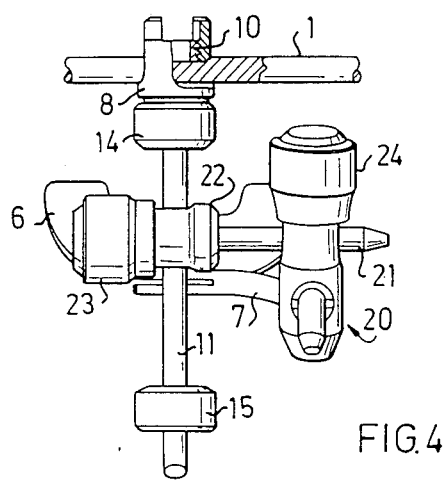
FIG. 4 is a front view on a larger scale than FIGS. 2 and 3 of the adjustment part of the face-bow device attached to the bow part.

As best shown in FIGS. 1 and 4 the support 8 is a practically cylindrical element having a central, axial through bore 9 and a transverse through canal (see FIG. 4) adapted to receive the bow 1. The bore 9 has two sections having different diameters, the upper section having larger diameter than the lower. The upper section extends from the upper end of the support 8 to the upper part of the bow 1 when placed in the canal.

The bow 1 is locked in the support 8 by a locking ring 10 having threads on its outside adapted to threads in the upper part of the bore 9. As mentioned the support 8 must have a certain angular orientation to the bow plane, suitably 90 degrees. Therefore, the bow 1 has its side turned to the ring 10 plane in order to guide the support to take this orientation when the ring 10 is tightened. This is done at the factory and this connection may also then be sealed.

The diameter of the lower section of the bore 9 is adapted to the diameter of a pin 11 belonging to the adjustment part of the face-bow device detachable from the bow means 1. The pin 11 has, adjacent each end, a lock washer 12, 13 fixed in slots in pin 11. A cup-shape locking nut 14, 15 surrounds each washer 12, 13. Each nut has its wider, open side turned outwardly and has a knurled outside. The inside diameter and threads of the upper nut 14 are adapted to the outer diameter and threads of the upper part of the support 8.

As best shown in FIG. 1 the upper and the lower part of the pin 11 have a bevel cut end 16 and 17, respectively. These ends are cut in the same manufacturing operation either simultaneously or consecutively in order to make sure that they have an exact angular orientation to each other.

The upper end 16 contacts the bow 1 when inserted into the bore 9 and the locking nut 14 is screwed to the lower part of the support 8. When then the locking nut 14 is tightened the bevel end 16 guides the pin 11 to be seated in a predetermined angular orientation and to be held firmly to the bow means. The upper part of the pin 11 has also a longitudinal guiding cut 18 and the support 8 a guiding screw 19 in order to prevent the pin 11 from being 180° incorrectly seated in the bore 9.

As best seen in FIGS. 3 and 4 the bite fork pin 7 is insertable in a first transverse bore in a locking clamp 20 for the bite fork. The locking clamp 20 has a second transverse bore perpendicular to the first bore and at another height position. A pin 21 extending from the end of a locking clamp 22 for the height position is inserted through the second transverse bore in the locking clamp 20. The locking clamp 22 has a transverse through bore, in which the pin 11 is seated, and is locked to or unlocked from the pin 11 by turning the knurled thumb nut 23.

The locking clamp 20 for the bite fork pin 7 may have a separate thumb nut both for locking the locking clamp 20 to the pin 21 and for locking it to the bite fork pin 7. This is not shown in any of the figures. However, in order to have as few adjusting move as possible, the locking clamp 20 in the shown embodiment, has only one knurled thumb nut 24 for locking both the pins 21 and 7 in just one operation. Both the locking clamps 20 and 22 are of a construction well known in the art and are therefore not described in detail.

The pin 11, the bite fork 6 with its pin 7 and the two locking clamps 20, 22 and the locking nuts 14 and 15 is the adjustment part, which is sent to the lab after registration on a patient.

Figure 5:
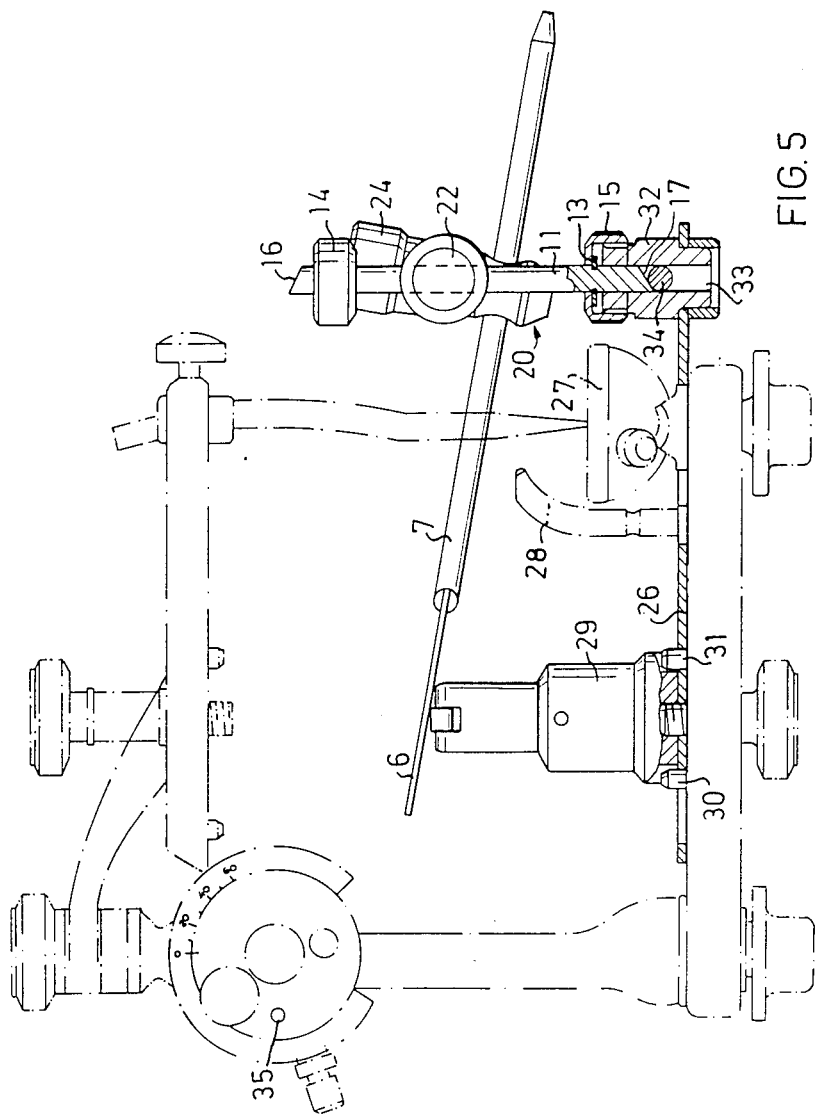
FIG. 5 is a side view of the adjustment part of the face-bow device mounted on an articulator.

As seen in FIG. 5 the articulator is provided with a detachable jig plate 26 plaved on its base plate. In respect to this base plate holes must be provided in the plate 26 around protruding elements and to give for elements to be attached to the base plate, such as the spring-loaded, tilting, telescopic bite fork support 29, the incisial table 27 and the guide table 28. The jig plate 26 can be guided to exact position by protruding elements on the base of the articulator, such as the pins 30 and 31 but other arrangements are possible, such as screwed joints or the like. The essential feature is that a jig means 32 is connected to the plate 26 in its front end. The jig means 32 has a cylindrical form and has an axial bore 33, which diameter is adapted to the diameter of the pin 11. The support 33 has also its upper outer part provided with threads and adapted to the inner diameter and threads of the lower locking nut 15 on the pin 11.

The jig means 32 has a transverse through bore in which a plug 34 having practically the same diameter as the pin 11 is inserted. The protruding lower end of the pin 11 is long enough to reach the plug 34 when inserted in the bore 33 from above with the locking nut 15 threaddedly connected to the outside of the jig means 32. Thereby a firm, angularly guided connection between the jig means 32 and the pin 11 can be obtained.

It is to be observed that the plug 34 need not be cylindrical, even if this is to be preferred, but can have another section than round, for instance squared.

It is to be noted that the guidance form of the ends 16 and 17 of the pin 11 could have other forms than being obliquely cut, such a V-form or U-form, but just having it obliquely cut is very simple and gives just as good a performance as other guidance forms.

The length of the pin 11 is chosen such that when connected in the jig means 32 its upper end extends to such a height as it would be if the bow means 1 were properly seated with its ends connected to the condylar pins 35.

The pin is strictly vertical in the embodiment shown in the Figures. This to be preferred. However, it is quite possible to have a slight oblique orientation of the pin 11 and hence the support 8 and the jig means 32, if only this is made alike for both the support and the jig and the pin length and the configuration of the bow means 1 is adapted to this orientation. The important feature is that the adjustment device has exactly the same position when placed on the articulator as it would have if it had been placed on the articulator together with its bow means 1.

Figure 2:
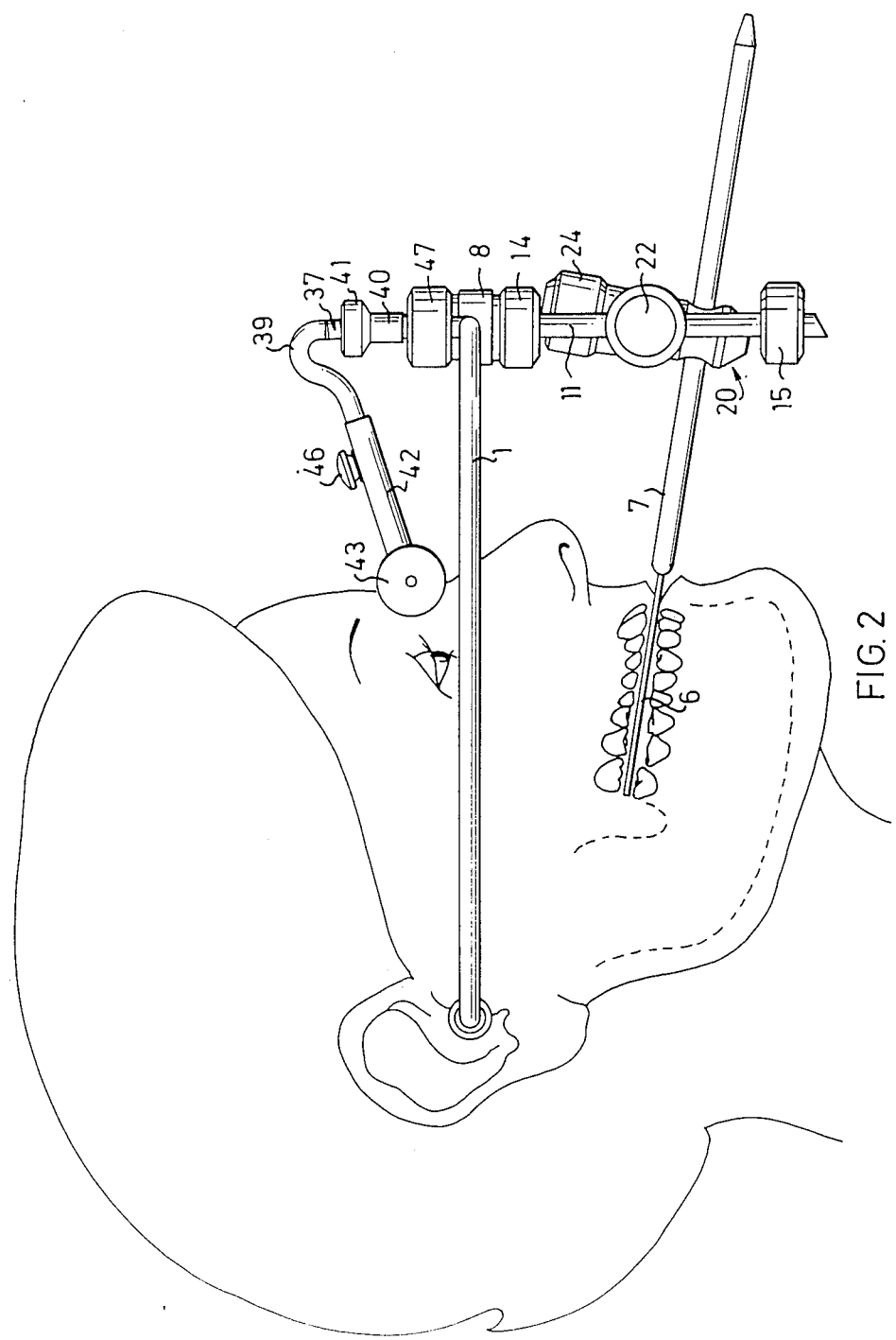
FIG. 2 is a side view of the face-bow device shown in FIG. 1, but on a smaller scale, mounted on a person.

As seen in FIGS. 1 to 3 a nose support is mountable on the top of the face-bow device just above the adjustment part 11 to 24. The nose support includes a rod having straight end sections 37 and 38 and a curved part 39 therebetween. The lower end of the section 37 is shown at 36. The end sections 37 and 38 have a certain mutual angular orientation, such that when the end section 37 is mounted vertically with the curved part 39 up, the end section 38 is sloping down, at an angle of for instance 20 degrees to a horizontal plane. The curved part 39 is essentially formed as a part of a circle having a sector angle substantially greater than the angle between the sections 37 and 38.

A cylindrical sleeve 42 is telesocpically mounted over a part of the other end section 38. The sleeve 42 has a nose resting device 43 asapted to be seated on the patient at the juncture of the upper portion of the nose and the forehead and to be comfortable for the patient. The device 43 can have a variety of forms of which one is shown in the figures. A pressure spring 44 is inserted in the sleeve 42 between the outer end of the end section 38 and some end stop (not shown) in the sleeve 42. The sleeve 42 has an elongated opening 45 in the part of it telescopically mounted on the end section 38. A locking screw 46 is inserted in a threaded bore in the end section 38 through the elongated opening 45.

the lowest part 36 of the section 37 has a cupformed nut 47 of practically the same configuration as the nuts 14 and 15 and has its inner diameter and threads adapted to the outer diameter and threads on the upper part of the support 8. The nut 47 is held against falling out by a swivel unit including a hollow cylinder 48 having a smooth inside and outside. The lower part 36 of the section 37 is shown inserted in the through opening of the cylinder 48. The outer diameter of the lower part of the sylinder 48 is less than the inner diameter of the top of the support 8. The cylinder 48 has a top neck section over which the opening of the nut 47 is placed, said opening having a greater diameter than the outer diameter of the neck section but a lesser diameter than the lower part of the cylinder 48. The neck section is inserted in the lower part of a nut 40 having a knurled wider top part 41 acting as a thumb wheel. The nut 40 and the neck section of the cylinder 48 are connected together against mutual movement in axial direction by a spring clip inside the lower part of the nut (not shown) in a way well known to those skilled in the art. The section 37 has threads along its whole length. The nut 40 has threads mating the threads on the section 37 at the inside of its upper part and is threaded on the section 37. When the thumb wheel 41 is rotated the nose support will be raised or lowered depending upon the rotating direction. However, it is to be noted that any extendable connection which is adjustable by a thumb wheel can be provided instead, such as for instance an arrangement of bottle screw of turn buckle type or the like.

When making registration of a patient's face the operator first sees to it that the sleeve 42 is locked in its innermost position and adjusts the ear pieces in the way described above. The bite fork 5 with its pin 7 is not yet mounted on the face-bow device and the operator now places the bite-fork device provided with a wax index into the patient's mouth and asks him to bite the fork and to keep biting. The clamps 20 and 22 on the adjustment device connected to the bow means 1 are loosened. The operator now sets the end of the bite fork pin 7 into the first transverse bore in the locking clamp 20 and moves the face-bow device in the direction of the face to move the pin 7 through the bore and bends out the arms of the bow means 1 to move the ear pieces 2 on the bow ends over the sides of the patint's face to place them into the ear meatuses. At this time the nose resting device 36 to 46 is turned to the side.

Then the operator holds the bow means 1 lifted by one hand such that it is approximately horizontal, turns the nose support towards the patient's face, loosens the locking screw 46 with his other hand so that the sleeve 42 with the nose support device 43 is pushed out by the spring 44 and moves the bow slightly in verticl direction to have the device 43 properly seated on the upper part of the nose and tightens the screw 46. The spring 44 is strong enough to just push out the device 43 but weak enough to stop pushing to any noticeable extent when the device 43 has reached the nose.

After that the bow means is moved vertically to rest in the orbital plane, which is a plane through the hinge axis points and the so-called orbital point under the eye of the patient. This is preferably done by the operator sighting at the patient's orbital point from the side and turning the nut 40 to raise or lower the bow means 1 to the exact position. The essential feature is that this adjustment can be made by only one hand in an easy way when sighting at the same time.

Thereafter the operator tightens the clamps 20 and 22. Then the registration is ready and the face-bow device is demounted from the patient and the adjustment part 11, 20, 22 with the bite fork means 6, 7 is demounted from the bow and sent to the lab.

Although a preferred embodiment of the present invention has been illustrated herein, it is to be understood that various changes and modifications may be made in the construction and arrangement of elements without departing from the spirit and scope of the invention as defined. For instance the bow in face-bow devices of any type, i.e. also of the type not having the bow lying in the orbital plane, can be provided with bow legs resiliently outbendable enough to permit bows having ear pieces adjusted to a suitable distance from each other to fit into the patient's ear meatuses to be passed over the patient's face before the ear pieces are inserted into the ears or to a suitable distance to be seated pressed against the hinge axis points.

I claim:

1. A face-bow device for registration of a patient's face and for transferring the registration to an articulator, for use in making dentures or parts thereof, including:
    a bite fork on a bite fork support;
    an adjustment means, in which said bite fork support is insertable,
    a bow means extending from ear to ear in front of said patient's face, on which bow means said adjustment means is mountable,
    said bow means having two arms firmly connected to each other, each arm having an integral, inwardly bent free end provided with an ear piece adapted to be placed in said patient's ear meatus, said free ends being aligned, said ear pieces being adjustably mounted directly on said free ends and adjustable toward and away from each other relative to said free ends,
    said arms being made of a resilient material and having sufficient resiliency to be resiliently outbendable at least to such an extent that a bow means having its free ends at a distance from each other adapted to the distance between the openings to said patient's ear meatuses in outbent condition is movable over the sides of said patient's face for placing said ear bow ends into said patient's ear meatuses, and thereafter, when removed from the patient, to return to its original shape of said bow.

2. A device according to claim 1, wherein said bow means is outbendable to a maximum extent lying between 10 and 50 mm, preferably ca 25 mm.

3. A device according to claim 1, wherein each ear piece is displaceable in longitudinal direction within a predetermined region and lockable at several locations along said region.

4. A device according to claim 1, wherein said adjustment means is a separate unit detachably mounted on said bow means and includes a pin on which a first clamping means connected to holding means for said bite fork pin is displaceably mounted, wherein a first support means mounted on said bow means has a tubular opening for said pin to be inserted therein, a part of said bow being transversely oriented to said opening at its inner limit, said pin having a first end formed to guidingly mate with said bow means part serving as said limit in said opening to give a predetermined orientation of said pin around its axis, and wherein a first manually adjustable locking means is adapted to draw said pin into its most inserted position in said opening in said first support means and to lock it in this position at adjustment to locking condition.

5. A device according to claim 4, wherein a jig means is arranged on the lower part of said articulator, said jig means having a tubular opening and a plug placed transverse to said opening and forming the bottom of it, wherein said pin has its second end formed to guidingly mate with the form of said plug to give a predetermined angular orientation of said pin around its axis when mounted in said jig means, and wherein a second manually adjustable locking means is arranged to draw said pin into its most inserted position in said opening in said jig means and lock it there at adjustment to locking condition.

6. A device according to claim 4, wherein said pin has an oblique first end.

7. A device according to claim 5, wherein said pin has an oblique second end.

8. A device according to claim 4, wherein said holding means includes a second clamping means having a manually operated adjustment means operable to lock said bite fork pin in its position and said holding means in relation to said first clamping means in one operation.

9. A nose support device to be mounted on a face bow device, including:
- nose resting means,
- holding means having a first and a second arm having between them a predetermined angle of less than 90 degrees,
- means on said first arm to attach said first arm to said bow device,
- manually operable means on said first arm to change the length of said first arm,
- said nose resting means being disposed on the end of said second arm,
- spring-loaded means on said second arm to make said second arm extendable, and
- manually operable locking means on said second arm to lock said spring-loaded means in a selected extended position and to unlock said spring-loaded means to change the length of said second arm.

10. A device according to claim 9, wherein a bow-formed section, having a sector angle substantially greater than said angle between said arm orientations, connects said extendable arms to each other.

11. A device according to claim 9, wherein a locking device is provided on said first arm to lock it in an upright position on said bow device, and said first arm has a part extendable in relation to said locking device having a thumb wheel to be rotated by an operator for extension or reduction of the arm length.

12. A device according to claim 9, wherein said second arm is extendable by means of a sleeve telescopically displaceable on a support arm means, said nose resting means being provided on said sleeve, wherein a manually adjustable locking means is provided to lock or unlock a set position of said sleeve on said support arm means, and wherein a weak spring is provided in said sleeve between the end of said second support arm means and an end stop in said sleeve.

* * * * *